United States Patent [19]
Erman et al.

[11] Patent Number: 6,114,565
[45] Date of Patent: Sep. 5, 2000

[54] PROCESS FOR OBTAINING NITRILES

[75] Inventors: Mark B. Erman, Atlantic Beach; Joe W. Snow; Melissa J. Williams, both of Jacksonville, all of Fla.

[73] Assignee: Millennium Specialty Chemicals, Jacksonville, Fla.

[21] Appl. No.: 09/390,508

[22] Filed: Sep. 3, 1999

[51] Int. Cl.$^7$ .................................................. C07L 253/00
[52] U.S. Cl. ............................................................ 558/315
[58] Field of Search .............................................. 558/315

[56] References Cited

U.S. PATENT DOCUMENTS

| | | |
|---|---|---|
| 2,933,506 | 8/1960 | Ohloff et al. . |
| 3,907,321 | 9/1975 | Hall et al. . |
| 3,911,018 | 10/1975 | Hall et al. . |
| 3,929,677 | 12/1975 | Hall et al. . |
| 4,202,837 | 5/1980 | Williamson . |
| 4,250,338 | 2/1981 | Sprecker et al. . |
| 5,214,160 | 5/1993 | Ertzweiler et al. . |
| 5,457,222 | 10/1995 | Oku et al. . |
| 5,514,830 | 5/1996 | Oku et al. . |
| 5,707,961 | 1/1998 | Baggrowicz et al. . |

FOREIGN PATENT DOCUMENTS

| | | |
|---|---|---|
| 464357B1 | 1/1992 | European Pat. Off. . |
| 743297A1 | 11/1996 | European Pat. Off. . |
| 40992 | 2/1994 | Japan . |
| 896039 | 5/1962 | United Kingdom . |

OTHER PUBLICATIONS

G. Ohloff, Liebigs Annalen der Chemie, Bd. 606, S. 100–123 (1959).

M. Mousseron–Canet et al., Bull. Soc. Chim. France, pp. 601–606 (1959).

G. Ohloff, *Zur Thermischen Isomerisation von Citral*, Tetrahedron Letters No. 11, pp. 10–14 (1960).

Brackman et al., *New Synthesis of Nitriles*, Chemical Abstracts, vol. 59 (1963).

Smith, et al., *Oxidation of Aldehyde N, N–Dialkylhydrazones with Hydrogen Peroxide. A New Nitrile Synthesis*, J. Org. Chem., vol. 31, pp. 4100–4102 (1966).

Misono, et al., *On the Formation of Benzonitrile from Benzaldehyde and Ammonia*, Bulletin of the Chemical Society of Japan, vol. 40, pp. 912–919 (1967).

G. Ohloff, *Chemistry of Odoriferous and Flavoring Substances*, Fortschritte der Chemischen Forschung, Bd. 12/2, pp. 185, 190–194 (1969).

Ohta, et al., *Benzimidoyl Radicals: Free–radical Reactions of Benzaldimines*, Chemical Communications, p. 1601 (1970).

Miller et al., *A Convenient, High–Yield Conversion of Aldehydes to Nitriles*, J. Org. Chem. vol. 40, No. 1, pp. 126–127 (1975).

Katritzky et al., *Heterocycles in Organic Synthesis*, J.C.S. Perkin I, pp. 1957–1960 (1979).

Olah et al., Synthesis, pp. 112–113 (1979).

G. Tennant, *Imines, Nitrones, Nitriles, and Isocyanides*, Comprehensive Organic Chemistry, vol. 2, pp. 385, 533–590 (1979).

Cathala et al., *Ammoxydation catalytique des hydrocarbures et reactions apparentees*, Bull. Soc. Chim. France, pp. 173–178 (1979).

Schirmann, et al., *Hydrogen Peroxide in Organic Chemistry*, Édition et Documentation Industrielle: Paris, pp. 23, 37; 79–87 (1979).

Cacchi, et al., *Amides from Nitriles using Basic Hydrogen Peroxide under Phase–Transfer Catalysed Conditions*, Synthesis, pp. 243–244 (1980).

Card et al., *Gas–Phase Synthesis of Nitriles*, J. Org. Chem., vol. 46, pp. 754–757 (1981).

Said, et al., Synthesis, pp. 223–224 (1989).

B. M. Andreev et al., Pischevaya Promyshlennost, N 11, pp. 55–56 (1990).

Yamazaki et al., *A Catalytic Synthesis of Nitriles from Aldehydes and Alcohols in the Presence of Aqueous Ammonia by Oxidation with $NiSO_4$–$K_2S_2)_8$*, Chemistry Letters, pp. 571–574 (1990).

B.M. Andreev et al., Zh. Org. Khim., V. 27(2), pp. 413–414 (1991).

Yuan and Peng, Chinese Chemical Letters, vol. 3, No. 7, pp. 507–510 (1992).

J. Mlochowski, et al., *Oxidation of Azomethine Compounds*, Polish Journal of Chemistry, vol. 66, pp. 1901–1928 (1992).

Müller and Lamparsky, eds. Blackie Academic & Professional, London–New–York–Tokyo–Melbourne–Madras, p. 197 (1994).

G. Fráter et al., 213th ACS National Meeting San Francisco, Apr. 13–17, Books of Abstracts, Part 2, p. 147 (1997).

J. Mlochowski, *Some Oxidative Transformations of the Carbonyl Compounds and their Azomethine Derivatives*, Chem. Papers, vol. 52(1), pp. 45–51 (1998).

Primary Examiner—Joseph McKane
Assistant Examiner—Joseph Murray
Attorney, Agent, or Firm—Needle & Rosenberg, P.C.

[57] ABSTRACT

A process for obtaining a nitrile represented by formula RCN, comprising contacting a corresponding aldehyde represented by formula RCHO with (i) ammonia or ammonium hydroxide, and (ii) hydrogen peroxide, in the presence of a transition metal or a transition metal compound.

26 Claims, No Drawings

PROCESS FOR OBTAINING NITRILES

FIELD OF THE INVENTION

The invention relates to a process for obtaining nitrites—compounds useful in practically all branches of practical organic chemistry. More specifically, the present invention relates to a process for obtaining nitrites RCN from aldehydes RCHO with the same number of carbon atoms and the same structure of the substituent R.

BACKGROUND OF THE INVENTION

The traditional two-stage method for obtaining nitrites from the corresponding aldehydes consists in the oximation of an aldehyde with hydroxylamine followed by dehydration of the resulting aldoxime using various dehydrating agents such as acetic anhydride, phosphorus pentoxide, dicyclohexylcarbodiimide, etc. (Scheme 1). See: G. Tennant, "Imines, Nitrones, Nitriles, and Isocyanides" in: Comprehensive Organic Chemistry, ed. I. O. Sutherland. Pergamon Press, Oxford, New York, Toronto, Sydney, Paris, Frankfurt, 1979, Vol. 2, pp. 385–590 (especially pp.533–537), and references therein. Recently, alkali metal hydroxides were patented as the dehydrating agents for this process (M. Oku and Y. Fujikura, U.S. Pat. No. 5,457,222 and U.S. Pat. No. 5,514,830).

Scheme 1

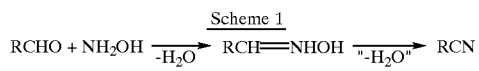

Modifications of this general method exist which allow "one-pot" preparation of nitrites, without the separation of intermediate oxime (see G. A. Olah and T. Keumi, Synthesis, 1979, pp.112–113, and references therein).

Also, methods are known based on the intermediacy of other N-substituted azomethine derivatives of aldehydes, such as 0-2,4-dinitrophenyl oximes (M. J. Miller and G. M. Loudon, J. Org. Chem., 1975, vol. 40, pp. 126–127), alkylideneaminopyridones (A. R. Katritzky and P. Molina-Buendia, J. Chem. Soc. Perkin I, 1979, pp.1957–1960), etc., where the intermediates are converted into nitrites by the non-oxidative methods.

A number of methods are based on the oxidative conversion of N-substituted azomethine derivatives of aldehydes. For example (Scheme 2a), N-t-butyl benzaldimine was oxidized into benzonitrile by diisopropyl peroxydicarbonate DiPPDC (H. Ohta and K. Tokumaru, J. Chem. Soc. Chem. Commun., 1970, p. 1601). Dimethylhydrazones (Scheme 2b) were oxidized to nitrites with meta-chloroperbenzoic acid (MCPBA), or in lower yields with hydrogen peroxide in the presence of selenium compounds (S. B. Said et al., Synthesis, 1989, pp. 223–224). Certain types of aromatic dimethylhydrazones can be oxidized with methanolic hydrogen peroxide without catalyst (R. F. Smith et al, J. Org. Chem., 1966, vol. 31, pp. 4100–4102). Reactions of this type were reviewed by J. Mlochowski in Chem. Papers, 1998, vol. 52(1), pp. 45–51 and by J. Mlochowski and S. B. Said in: Polish Journal of Chemistry, 1992, vol. 66, pp. 1901–1928.

Scheme 2

(a)

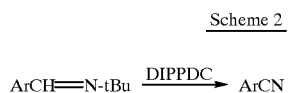

(b)

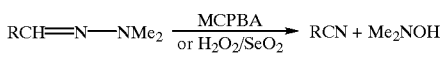

All the above shown methods have a mutual disadvantage, namely the use of relatively expensive hydroxylamine, dimethylhydrazine, etc. Methods based on the use of inexpensive ammonia are more attractive from the practical standpoint. The latter methods involve the formation of aldimine intermediate followed by its dehydrogenation or oxidative dehydrogenation according to Scheme 3 (ammoxidation).

Scheme 3

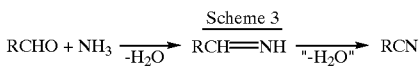

Practical value of these methods depends largely on the reagent used for the oxidative dehydrogenation. For instance, there is a method based on the use of potassium persulfate in the presence of nickel salts and aqueous ammonia (S. Yamazaki and Y. Yamazaki, Chem. Lett., 1990, pp. 571–574). The procedure gives 21–76% yields of aromatic and unsaturated nitrites from the corresponding aldehydes, including a 48% yield of geranyl nitrile from citral (Scheme 4).

Scheme 4

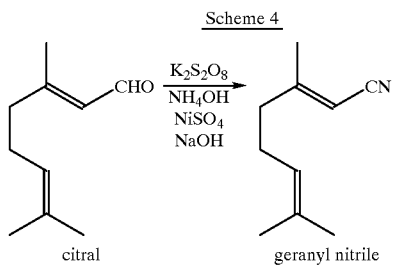

citral      geranyl nitrile

Practical applicability of this method is restricted mostly because it requires 1.5–2.0 moles of potassium persulfate per one mole of the aldehyde, which means 540.6 weight parts of the persulfate per 152.2 weight parts of citral.

In a number of ammoxidation procedures, air or oxygen are used as dehydrogenating agents for the aldimine intermediates according to Scheme 3. These procedures can be classified into two groups: 1) gas phase/high temperature, and 2) liquid phase/low temperature processes.

In a Group 1 process, propanal is converted into a mixture containing some propionitrile and acrylonitrile together with acetonitrile, aldehydes, and other by-products by a reaction with gaseous ammonia and air at 460° C. over Sn/Sb oxide catalyst (M. Cathala, et al., Bull. Soc. chim. France, 1979, pp. 173–178). In another example (R. J. Card and J. L. Schmitt, J. Org. Chem., 1981, vol. 46, pp. 754–757), benzonitrile, p-methoxybenzonitrile, and octanenitrile are obtained in good yields by passing a stream of gaseous ammonia containing 5 mol % of the corresponding aldehyde through a catalyst bed (3 cm of Cu/alumina) at 325° C. According to Brit. Pat. 709,337, acrolein is converted into acrylonitrile in a gas phase reaction with air/ammonia/steam/ nitrogen mixture over molybdenum catalysts at 285–445° C.

A major disadvantage of the Group 1 processes is the high temperature which can affect thermally labile aldehydes and nitrites. For example, according to G. Ohloff, Tetrahedron Lett., 1960, p. 10–14, citral undergoes various isomerization and cyclization reactions already at 130–205° C. Another disadvantage of the Group 1 processes is the use of large excess of ammonia.

In Group 2 methods, reactions of aldehydes with ammonia and oxygen occur in the liquid phase in the presence of copper compounds. Again a significant excess of ammonia is used, and the reaction mixture is strongly diluted with a solvent. W. Brackman and P. J. Smit (Rec. Trav. Chim., 1963, vol. 82(8), pp. 757–762) reported a method for obtaining nitriles by treating aldehydes (0.05 moles) with oxygen at 30° C. in 100 ml of methanol containing 0.4 moles (eight-fold excess) of ammonia, 0.03 moles of sodium methoxide, and 4 mmoles of copper(II) chloride. A detailed study of the reaction using benzaldehyde as starting material was conducted by A. Misono et al. (Bull. Soc. Chem. Japan, 1967, vol. 40, pp. 912–919) at even stronger dilution: 0.03 moles of benzaldehyde and about 0.09 moles of ammonia in about 100 ml of methanol. A process for ammoxidation of acrolein comprising pretreatment of a copper salt with ammonia followed by contacting the obtained complex with acrolein in the presence of oxygen was patented in U.S. Pat. No. 4,202,837. Best yields of acrylonitrile 29–40% were obtained with a molar ratio acrolein:CuBr=1.05–1.2 (examples 2 and 5) which means over twofold excess of the catalyst by weight, and this process is stoichiometric rather than catalytic.

Various known syntheses of nitriles are summarized in the most recent comprehensive reviews: M. North, "General methods and aliphatic nitriles" in: Comprehensive Organic Functional Group Transformations. Ed. A. Katrizky et al.; Elsevier: Oxford, UK; 1995, Vol. 3, pp. 610–640, 733–856; M. J. Kiefel, "α,β-Unsaturated and aryl nitriles", ibid., pp. 641–676, 733–856.

SUMMARY OF THE INVENTION

In accordance with the purpose(s) of this invention, as embodied and broadly described herein, this invention, in one aspect, relates to a process for obtaining a nitrile comprising contacting an aldehyde with (i) ammonia or ammonium hydroxide, (ii) hydrogen peroxide, and (iii) a transition metal or transition metal compound wherein the contacting is performed sequentially, simultaneously, or in any order.

We found no patents or other publications describing a process for obtaining nitriles by reacting corresponding aldehydes with ammonia and hydrogen peroxide. Even more, the very existence of such a process seemed unlikely based on the available information. First, it is known that carbonyl compounds react with hydrogen peroxide in the presence of ammonia to give, depending on the reaction conditions, aminoperoxides, derivatives of hydrazine or hydroxylamine, but not nitriles. Second, hydrogen peroxide can oxidize aldehydes to formates (the Baeyer-Villiger reaction), which can hydrolyse to give alcohols or phenols. Oxidation of aldehydes to acids is also possible. Third, nitriles themselves can react with hydrogen peroxide providing iminoperacids, which can further react with a second molecule of hydrogen peroxide to form amides. One more undesirable reaction could be expected with unsaturated starting aldehydes—epoxidation of the double bond. See: J. P. Schirmann and S. Y. Delavarenne, "Hydrogen Peroxide in Organic Chemistry," Edition et documentation industrielle: Paris, 1979, p. 23, 37; 79–87, and references therein. S. Cachhi et al., Synthesis, 1980, pp. 243–244. C. H. Hassall, The Baeyer-Villiger oxidation of aldehydes and ketones. Organic Reactions, 1957, vol. 9, pp. 78–106.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of preferred embodiments of the invention and the Examples included therein.

Definitions and Use of Terms

It must be noted that, as used in the specification and the appended claims, the singular forms "a," "an" and "the" include plural referents unless the context clearly dictates otherwise. Thus, for example, reference to "a transition metal" includes mixtures of transition metals, reference to "a solvent" includes mixtures of two or more solvents, and the like.

Ranges are often expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

The term "alkyl" as used herein refers to a cyclic, branched or unbranched saturated hydrocarbon group, such as methyl, ethyl, n-propyl, isopropyl, n-butyl, isobutyl, t-butyl, octyl, decyl, tetradecyl, hexadecyl, eicosyl, tetracosyl and the like.

The term "alkoxy" as used herein intends an alkyl group bound through a single, terminal ether linkage; that is, an "alkoxy" group may be defined as —OR with R being alkyl.

The term "alkenyl" as used herein intends a hydrocarbon group having one, two, or more double bonds, and thus includes alkadienes. When appropriate, structures such as (AB)C=C(CD) are intended to include both the E and Z isomers. This may be presumed in structural formulae herein wherein an asymmetric alkene is present, or it may be explicitly indicated by the bond symbol—.

"Alkynyl" refers to a cyclic, branched or unbranched hydrocarbon group that contains one or more triple bonds.

"Aryl" refers to a hydrocarbon group whose molecules have the ring structure characteristic of benzene, naphthalene, phenanthrene, anthracene, etc., i.e. either the six carbon ring of benzene or the condensed six carbon rings of the other aromatic derivatives. For example, an aryl group may be phenyl $C_6H_5$ or naphthyl $C_{10}H_7$.

"Heteroaryl" designates a closed ring structure, usually of either five or six members, in which one or more of the atoms in the ring is a heteroatom such as sulfur, nitrogen, oxygen, etc., including pyridine, pyrrole, furan, thiophene, and purine. "Transition metal" refers to any one of the elements in Groups 1B–VIIB and VIII of the periodic table, and preferably refers to copper, iron, cobalt, nickel, manganese, silver, or palladium.

"Citral" refers to 3,7-dimethyl-2,6-octadienal.
"Geranial" refers to the 2-E isomer of Citral.
"Neral" refers to the 2-Z isomer of Neral.
"Citronellal" refers to 3,7-dimethyl-6-octenal.

Discussion

We have now discovered that nitriles can be obtained by reacting corresponding aldehydes with ammonia and hydrogen peroxide in the presence of transition metals or transition metal compounds. Thus, in one aspect the invention provides a process for obtaining a nitrile comprising contacting an aldehyde with (i) ammonia or ammonium hydroxide, (ii) hydrogen peroxide, and (iii) a transition metal or transition metal compound wherein the contacting is performed sequentially, simultaneously, or in any order.

The nitrile is preferably represented by formula (1),

RCN        (1)

and the aldehyde represented by formula (2),

RCHO        (2)

wherein: R represents alkyl, alkenyl, alkynyl, aryl, arylalkyl, alkylaryl, arylalkenyl, alkenylaryl, alkynylaryl, arylalkynyl, heteroaryl, alkylheteroaryl, heteroarylalkyl, alkenylheteroaryl, or heteroarylalkenyl; R is branched, linear, cyclic, and/or polycyclic; R is optionally substituted with one or more functional groups selected from hydroxy, alkoxy, carboxy, cyano, alkoxycarbonyl, and carbonyl.

R preferably comprises from about I to about 40 carbon atoms, and even more preferably from about 5 to about 20. When the functional group comprises an alkyl group, the alkyl group preferably comprises no more than 30 carbons, and even more preferably comprises no more than 20 carbons.

Preferred aldehydes for performing the process of this invention include, in separate embodiments: (1) citral, geranial, and neral, (2) cinnamaldehyde, piperonal, benzaldehyde, p-methoxybenzaldehyde, and 2,4-hexadienal, and (3) the (3R)-enantiomer of citronellal, the (3S)-enantiomer of citronellal, and mixtures thereof.

Preferred transition metals and transition metal compounds include copper metal, copper salts and copper complexes. Other preferred transition metals include iron, cobalt, nickel, manganese, silver, palladium, etc., and compounds thereof. The molar ratio of transition metal or transition metal compound to aldehyde is preferably from about 0.0001 to about 50, and more preferably from about 0.01 to about 1.

According to the invention, ammonia can be used as its aqueous solution (ammonium hydroxide) or fed in the gaseous form. Hydrogen peroxide is preferably used as its aqueous solution.

The process can be performed over a wide variety of conditions, and can be performed either continuously or batch-wise. Although the reaction generally proceeds regardless of the temperature, addition sequence, and the addition rates of the reagents, all these parameters can generally be optimized to obtain higher yields of the nitriles. The reaction temperature may vary within a wide range. A preferred temperature range is minus 10° C. to +70° C., and a more preferred range of temperatures is from about 0° C. to +45° C.

The process is preferably performed with a molar ratio of ammonia or ammonium hydroxide to aldehyde of from about 0.5 to about 20, more preferably from about 0.9 to about 5, and even more preferably from about 1 to about 2. The process also is preferably performed with a molar ratio of hydrogen peroxide to aldehyde from about 0.8 to about 50. More preferably from about 1 to about 10.

The process can be realized in the presence of an organic solvent or without a solvent. Examples of solvents are:
1) alcohols such as methanol, ethanol, isopropanol, and higher alcohols;
2) glycols such as ethylene glycol, propylene glycol, diethylene glycol, triethylene glycol, and others;
3) mono and disubstituted glycol ethers such as methyl cellosolve, ethyl cellosolve, monoglyme, diglyme, 1-methoxy-2-propanol, and others;
4) esters such as ethyl acetate, butyl acetate, and others;
5) dimethylsulfoxide, acetonitrile, pyridine, dimethylformamide, N-methylpyrrolidinone, triethanolamine, and other solvents containing sulfur, nitrogen, phosphorus, or containing one of these elements and oxygen;
6) hydrocarbons such as hexane, heptane, cyclohexane, benzene, toluene, xylene, and others;
7) combinations of solvents.

When conducted in the presence of an organic solvent, the weight ratio of solvent to aldehyde is preferably from about 0.3 to about 25, and more preferably from about 1 to about 9. Also, the process can be run in a more or less diluted aqueous solution. The reaction can be run in the presence of a phase-transfer catalyst (long-chain tertiary or quaternary amine salts or free tertiary amines), or without a phase-transfer catalyst.

Various modes or sequences of addition/mixing of reagents can be used, for example:
1) addition of hydrogen peroxide to a mixture of an aldehyde, ammonia, catalyst and solvent, or the same without solvent;
2) simultaneous, parallel, or consecutive addition of an aldehyde, aqueous ammonium hydroxide, and hydrogen peroxide to a mixture of a solvent and a catalyst;
3) simultaneous, parallel, or consecutive addition of an aldehyde in a solvent, aqueous ammonium hydroxide, and hydrogen peroxide to a mixture of the same solvent, or another solvent, and a catalyst;
4) simultaneous, parallel, or consecutive addition of aqueous ammonium hydroxide and hydrogen peroxide to a mixture of an aldehyde and a catalyst;
5) feeding gaseous ammonia to a mixture of a solvent and a catalyst, with simultaneous, parallel, or consecutive addition of an aldehyde and hydrogen peroxide;
6) feeding gaseous ammonia to a mixture of a solvent, an aldehyde and a catalyst, with simultaneous or consecutive addition of hydrogen peroxide; and
7) others.

Thus, in one embodiment the contacting is performed by adding aldehyde, ammonia or ammonium hydroxide and hydrogen peroxide to a mixture of catalyst and solvent. In another embodiment the contacting is performed by adding ammonia or ammonium hydroxide and hydrogen peroxide to a mixture of aldehyde, solvent, and catalyst. In still another embodiment the contacting is performed by adding aldehyde, ammonia or ammonium hydroxide and hydrogen peroxide to a mixture of catalyst and solvent; addition of the aldehyde, ammonia or ammonium hydroxide, and hydrogen peroxide starts at about the same time; the addition of the aldehyde is completed first; the addition of the ammonia or ammonium hydroxide is completed second; and the addition of the hydrogen peroxide is completed third.

After completion of the reaction, the reaction mixture can be worked up in many ways. It is to be understood that, in each case, the optimum work-up procedure depends on the nature of the starting aldehyde and the resulting nitrile, or the solvent used, etc. For example, the mixture can be "quenched" with aqueous sodium sulfite or bisulfite, then diluted with water and an organic solvent. After separation of layers and optional extraction of the water layer, the solvent can be evaporated and the product distilled. Sometimes the product can be crystallized from the reaction mixture, as in the case of piperonylonitrile. Another possible method for the work up is filtration of the reaction mixture through a pad of a sorbent such as diatomaceous earth, or a pad of an inorganic salt such as sodium sulfate, magnesium sulfate, sodium sulfite and others, followed by evaporation of the solvent and distillation of the product.

After separation of the product, the catalyst can be reused. When it is desirable to reuse the catalyst, the reaction can be run in a water soluble solvent having a limited miscibility with hydrocarbons such as heptane. Examples of such solvents are: glycols, cellosolves, 1-methoxy-2-propanol, dimethyl sulfoxide, etc. After the completion of the reaction, the product can be extracted with a hydrocarbon, and the remaining solvent/water/catalyst layer can be reused after optional reconcentration. When it is not desirable to reuse the catalyst, the transition metal or its compound can be removed from waste water by converting it into an insoluble or poorly soluble compound such as, for example, a sulfide, a phosphate, or a complex with a chelating polymer.

Thus, the invention provides a convenient and highly practical process for obtaining nitriles from corresponding aldehydes. The advantages of the invention will be realized and attained by means of the elements and combinations particularly pointed out in the claims. It is to be understood that both the foregoing description of the invention and the following examples are not restrictive to the invention, as claimed.

EXAMPLES

The following examples are put forth so as to provide those of ordinary skill in the art with a complete disclosure and description of how the method for obtaining nitriles is realized, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Geranyl Nitrile from Technical Grade Citral.

To a stirred mixture of 400 ml of isopropanol and 1.0 g (0.01 mole) of cuprous chloride, at 17–23° C. was added dropwise 58 g (0.487 mole) of 29.4% aqueous ammonium hydroxide over a period of about 3 hours. Parallel to the addition of ammonium hydroxide, a mixture of 74.0 g (0.38 mole) of 78.1% technical grade citral (isomer ratio E/Z=2.4) and 1.0 g of hexadecane (internal standard) was added over a period of about 2.5 hours. Parallel to the additions of ammonium hydroxide and citral, 95 g (1.4 moles) of 50% aqueous hydrogen peroxide was added over a period of about 4 hours. After the additions were finished, the mixture was stirred for another hour, and GC analysis showed that the reaction mixture contained about 51 g of geranyl nitrile (0.343 mole), which corresponds to ~90% theoretical yield. After conventional work-up, the product was distilled to give 53.4 g of 88.2% purity geranyl nitrile (47.1 g; 0.3156 mole). Isomer ratio E/Z=2.4. Distilled yield 83.1% of the theory.

Example 2

Geranyl Nitrile from 95% Purity Citral with Molar Ratio Ammonium Hydroxide/citral=1:1.

To a stirred mixture of 300 ml of isopropanol and 1.0 g (0.01 mole) of cuprous chloride, at 17–27° C. was added dropwise 48 g (0.4 mole) of 29.4% aqueous ammonium hydroxide over a period of about 2.5 hours. Parallel to the addition of ammonium hydroxide, 64.0 g (0.399 mole) of 95% grade citral (isomer ratio E/Z=0.99) and 1.0 g of hexadecane (internal standard) was added over a period of about 2.5 hours. Parallel to the additions of ammonium hydroxide and citral, 95 g (1.4 moles) of 50% aqueous hydrogen peroxide was added over a period of about 4 hours. After the additions were finished, the mixture was stirred for another hour, and GC analysis showed that the reaction mixture contained about 49 g of geranyl nitrile (0.328 mole), which corresponds to ~82% theory yield. After conventional work-up, the product was distilled to give 47.3 g of 96.1% purity geranyl nitrile (45.5 g; 0.305 mole). Isomer ratio E/Z=1.2. Distilled yield 76.3% of the theory.

Example 3

Geranyl Nitrile from 95% Purity Citral with Molar Ratio Ammonium Hydroxide/citral=1.23:1.

To a stirred mixture of 400 ml of isopropanol and 1.0 g (0.01 mole) of cuprous chloride, at 17–22.5° C. was added dropwise 58 g (0.487 mole) of 29.4% aqueous ammonium hydroxide over a period of about 3 hours. Parallel to the addition of ammonium hydroxide, 63.4 g (0.396 mole) of 95% grade citral (isomer ratio E/Z=1.11) and 1.0 g of hexadecane (internal standard) was added over a period of about 2.5 hours. Parallel to the additions of ammonium hydroxide and citral, 95 g (1.4 moles) of 50% aqueous hydrogen peroxide was added over a period of about 4 hours. After conventional work-up, the product was distilled to give 48.5 g of 96.3% purity geranyl nitrile (46.7 g; 0.313 mole). Isomer ratio E/Z=1.33. Distilled yield 79.0% of the theory.

Example 4

Geranyl Nitrile from 2-E Citral (geranial).

To a stirred mixture of 300 ml of isopropanol and 1.0 g (0.01 mole) of cuprous chloride, at 17.1–22.2° C. was added dropwise 58 g (0.487 mole) of 29.4% aqueous ammonium hydroxide over a period of 200 mins. Parallel to the addition of ammonium hydroxide, 61.1 g (0.4 mole) of geranial (contains 98.5% of geranial and 1.1% of neral) and 1.0 g of hexadecane (internal standard) was added over a period of about 2.5 hours. Parallel to the additions of ammonium hydroxide and citral, 95 g (1.4 moles) of 50% aqueous hydrogen peroxide was added over a period of about 4 hours. After conventional work-up, the product was distilled to give 47.6 g of 96.6% total purity geranyl nitrile (46.0 g; 0.308 mole; contains 89.3% of 2-E-geranyl nitrile and 7.3% of 2-Z-geranyl nitrile). Distilled yield 77.0% of the theory.

Examples 5–19

Syntheses of Geranyl Nitrile from Citral using various Cu Catalysts and Solvents.

To a stirred mixture of 300 ml of a solvent and 0.01 mole of a catalyst (see Table 1) at 17–26° C. was added dropwise 53–58 g (0.44–0.49 mole) of 29.4% aqueous aiiimonium hydroxide over a period of about 3 hours. Parallel to the addition of ammonium hydroxide, a mixture of 74.0 g (0.38 mole) of 78.1% technical grade citral (isomer ratio E/Z=2.4) and 1.0 g of hexadecane (internal standard) was added over a period of about 2.5 hours. Parallel to the additions of ammonium hydroxide and citral, 95 g (1.4 moles) of 50% aqueous hydrogen peroxide was added over a period of about 4 hours. After the additions were finished, the mixture was stirred for another hour, worked up by stirring for 1 hour with 10% aqueous sodium sulfite, and diluted with water and heptane or chloroform. The organic layer was separated, the water layer was extracted with heptane or chloroform. After evaporation of the solvent, the product was distilled in vacuum. Distilled yields are given in Table 1.

TABLE 1

| Example | Catalyst | Solvent | Distilled yield of geranyl nitrile, % |
|---|---|---|---|
| 5 | Cu (I) chloride | Isopropanol | 82.8 |
| 6 | Cu (I) bromide | Isopropanol | 79.9 |
| 7 | Cu (I) iodide | Isopropanol | 56.3 |
| 8 | Cu (I) oxide | Isopropanol | 76.9 |
| 9 | Cu (I) acetate | Isoptopanol | 76.8 |
| 10 | Cu (II) chloride | Isopropanol | 80.0 |
| 11 | Cu (II) acetylacetonate | Isopropanol | 82.7 |
| 12 | Cu metal | Isopropanol | 75.8 |
| 13 | Cu (II) chloride | Dimethyl sulfoxide | 59.3 |
| 14 | Cu (II) chloride | Triethylene glycol | 45.3 |
| 15 | Cu (II) chloride | Methanol | 62.4 |
| 16 | Cu (II) chloride | 1-Methoxy-2-propanol | 81.0 |
| 17 | Cu (I) chloride | Propylene glycol | 59.9 |
| 18 | Cu (II) chloride | Diethylene glycol | 51.4 |
| 19 | Cu (II) chloride | N-methyl pyrrolidinone | 61.0 |

Examples 20–24

Synthesis of Geranyl Nitrile from Citral using Various Catalysts and Solvents.

These reactions were carried out in the same manner as examples 5–19, but yields were determined by GC. Results are given in Table 2.

TABLE 2

| Example | Catalyst | Solvent | GC yield of geranyl nitrile, % (based on citral taken into reaction) |
|---|---|---|---|
| 20 | Fe (II) acetylacetonate | Isopropanol | 3.0 |
| 21 | Mn (III) acetylacetonate | Isopropanol | 2.7 |
| 22 | Ag acetylacetonate | Isopropanol | 1.7 |
| 23 | Cu (II) chloride | Acetonitrile | 19.0 |
| 24 | Cu (I) chloride | Dimethylformamide | 22.1 |

Examples 25–27

Syntheses of Geranyl Nitrile in Dimethylformamide.

Aqueous ammonium hydroxide (concentration 29.4%, 15 g, 0.126 mole) was added at 8–15° C. over a period of 5–11 min to a stirred mixture of 16 g of 95% citral (0.1 mole; isomer ratio geranial/neral 0.96), 125 ml of dimethylformamide and 0.5 g of a catalyst specified in Table 3. Then, 30 g of 50% hydrogen peroxide (0.44 mole) was added over a period of 20–40 min while the temperature was maintained within about the same range. The mixture was stirred for another ~1.5 hour and analyzed by GC. Results are given in Table 3.

TABLE 3

| | | GC, % by normalization | | | |
|---|---|---|---|---|---|
| Example | Catalyst | Neryl nitrile | Geranyl nitrile | Unreacted neral | Uhreacted geranial |
| 25 | Copper (II) chloride | 29.4 | 50.1 | 1.3 | 2.0 |
| 26 | Cobalt (II) chloride | — | 2.5 | 1.5 | 2.3 |
| 27 | Nickel (II) chloride | — | 1.3 | 1.7 | 2.4 |

Examples 28–33

Synthesis of Geranyl Nitrile at Various Temperatures and Addition Times of the Reagents.

These reactions were carried out as in Example 2 but at different temperatures and addition times of the reagents. Reaction conditions and distilled yields of geranyl nitrile are given in Table 4.

TABLE 4

| | Temperature | Addition times of the reagents, in minutes | | | Distilled yields of geranyl nitrile, |
|---|---|---|---|---|---|
| Example | ° C. | Citral | NH$_4$OH | H$_2$O$_2$ | % of the theory |
| 28 | 8–16 | 147 | 147 | 236 | 61.4 |
| 29 | 6–13 | 152 | 149 | 228 | 39.7 |
| 30 | 5–13 | 188 | 123 | 240 | 45.9 |
| 31 | 7–18 | 155 | 133 | 240 | 49.4 |
| 32 | 6–15 | 132 | 140 | 240 | 54.5 |
| 33 | 15–23 | 145 | 157 | 250 | 73.4 |
| 2 | 17–26 | 150 | 155 | 235 | 76.3 |

Example 34

Synthesis of Geranyl Nitrile in 1-methoxy-2-propanol, with Reuse of the Solvent/water/catalyst Layer.

The reaction was carried out as in Example 16, then worked up by extraction with heptane. After evaporation of the heptane, the product was distilled to give 52.2 g of 88.3% geranyl nitrile; yield 81.3% of the theory. After the extraction, the solvent/water/ catalyst layer was reused, without reconcentration, in the next similar reaction. In the second run, the distilled yield of geranyl nitrile was 35.3% of the theory.

Examples 35–38

Syntheses of Trans-cinnamonitrile, 2,4-hexadienenitrile, Citronellyl Nitrile, and 2-methyl-2-pentenenitrile.

To a stirred mixture of 300 ml of isopropanol and 1.36 g of cupric chloride (0.01 mole) at 17–24° C. was added dropwise 58 g (0.487 mole) of 29.4% aqueous ammonium hydroxide over a period of about 3 hours. Parallel to the addition of ammonium hydroxide, a mixture of 0.4 mole of an aldehyde (Table 5) and 1.0 g of hexadecane (internal standard) was added over a period of about 2.5 hours. Parallel to the additions of ammonium hydroxide and citral, 95 g (1.4 moles) of 50% aqueous hydrogen peroxide was added over a period of about 4 hours. After the additions were finished, the mixture was worked up by stirring for 1 hour with 10% aqueous sodium sulfite, and diluted with water and heptane or chloroform. The organic layer was separated, the water layer was extracted with heptane or chloroform. After evaporation of the solvent, the product was distilled in vacuum. Distilled yields are given in Table 5.

Example 39

Synthesis of Piperonylonitrile (3.4-methylenedioxybenzonitrile) from Piperonal (3,4-methylenedioxybenzaldehyde).

To a stirred mixture of 200 ml of isopropanol and 1.36 g of cupric chloride at 17–23° C. was added dropwise 58 g (0.487 mole) of 29.4% aqueous ammonium hydroxide over a period of 190 min. Parallel to the addition of ammonium hydroxide, a solution of 601 g of 99% piperonal (0.396 mole) and 1.0 g of hexadecane (internal standard) in 100 ml of isopropanol was added over a period of 147 min. Parallel to the additions of ammonium hydroxide and piperonal, 150 g (2.2 moles) of 50% aqueous hydrogen peroxide was added over a period of 590 min. After the additions were finished, the mixture was worked up by stirring for 1 hour with 10% aqueous sodium sulfite, and diluted with water and chloroform. The organic layer was separated, the water layer was extracted with chloroform. After evaporation of the solvent, the weight of the crude solid product was 36.4 g (crude yield about 60%). Recrystallization of the crude from boiling heptane gave 17.9 g of crystalline piperonylonitrile; yield 30.7% of the theory.

Examples 40–44

Syntheses of p-methoxybenzonitrile, Benzonitrile, Trans-2-hexenenitrile, Crotononitrile, and Undecanenitrile.

The reactions were carried out as in examples 35–38, but yields were determined by GC (Table 6).

TABLE 5

| Example | Starting aldehyde (RCHO) | Product (RCN) | R | Distilled yield, % based on aldehyde taken into reaction |
|---|---|---|---|---|
| 35 | Cinnamaldehyde | Cinnamonitrile | $C_6H_5CH=CH-$ | 71.7 |
| 36 | Sorbic aldehyde | 2,4-Hexadienenitrile | $MeCH=CHCH=CH-$ | 52.8 |
| 37 | Citronellal | Citronellyl nitrile | $Me_2C=CHCH_2CH_2CMeCH_2-$ | 7.2 |
| 38 | 2-Methyl-2-pentenal | 2-Methyl-2-pentenenitrile | $MeCH_2CH=C(Me)-$ | 4.5 |

TABLE 6

| Example | Starting aldehyde (RCHO) | Product (RCN) | R | Yield, % (GC) based on aldehyde taken into reaction |
|---|---|---|---|---|
| 40 | Anisaldehyde | p-Methoxybenzonitrile | p-MeOC$_6$H$_5$— | 38.4 |
| 41 | Benzaldehyde | Benzonitrile | C$_6$H$_5$— | 23.6 |
| 42 | Trans-2-hexenal | Trans-2-hexenenitrile | MeCH$_2$CH$_2$CH=CH— | 17.8 |
| 43 | Crotonaldehyde | Crotononitrile | MeCH=CH- | 7.2 |
| 44 | Undecylic | Undecanenitrile | Me(CH$_2$)$_9$— | 6.0 |

Example 45

Synthesis of Geranyl Nitrile with Following Precipitation of the Catalyst.

To a stirred mixture of 300 ml of isopropanol and 1.0 g (0.01 mole) of cuprous chloride, at 17–23° C. was added dropwise 58 g (0.487 mole) of 29.4% aqueous ammonium hydroxide over a period of about 3 hours. Parallel to the addition of ammonium hydroxide, a mixture of 74.0 g (0.368 mole) of 75.7% purity technical grade citral, 1.0 g of hexadecane, and 25 ml of heptane was added over a period of about 2.5 hours. Parallel to the additions of ammonium hydroxide and citral, 95 g (1.4 moles) of 50% aqueous hydrogen peroxide was added over a period of about 4 hours. Following the addition of the 50% aqueous hydrogen peroxide, 50 g of 85% phosphoric acid was added and the resulting mixture was stirred for 1 hour, after which it was diluted with 175 ml of heptane and treated with 30 g of crystalline NaCl. The layers formed were separated, and the organic layer was distilled to give 54.0 g of 86.6% purity geranyl nitrile (46.8 g; 0.314 mole). The distilled yield was 85.2% of the theory.

The water layer was separated from the precipitate of copper phosphate and treated with 5 g of saturated aqueous solution of sodium sulfide. After separation from copper sulfide occurred, the water contained practically no copper.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A process for obtaining a nitrite comprising contacting an aldehyde with (i) ammonia or ammonium hydroxide, (ii) hydrogen peroxide, and (iii) a transition metal or transition metal compound wherein the contacting is performed sequentially, simultaneously, or in any order.

2. The process of claim 1 wherein the nitrite is represented by formula (1),

RCN    (1)

and the aldehyde is represented by formula (2),

RCHO    (2)

wherein:
   a. R represents alkyl, alkenyl, alkynyl, aryl, arylalkyl, alkylaryl, arylalkenyl, alkenylaryl, alkynylaryl, arylalkynyl, heteroaryl, alkylheteroaryl, heteroarylalkyl, alkenylheteroaryl, or heteroarylalkenyl;
   b. R is branched, linear, cyclic and/or polycyclic;
   c. R is optionally substituted with one or more functional groups selected from hydroxy, alkoxy, carboxy, cyano, alkoxycarbonyl, and carbonyl.

3. The process of claim 1 wherein the transition metal or transition metal compound is copper, a copper salt, or a copper complex.

4. The process of claim 1 wherein the contacting is carried out in the presence of an organic solvent.

5. The process of claim 1 wherein the contacting is carried out in the presence of an alcohol, glycol, or glycol ether.

6. The process of claim 1 wherein the contacting is carried out in the presence of isopropanol.

7. The process of claim 1 wherein the contacting is carried out in the presence of 1-methoxy-2-propanol.

8. The process of claim 1 wherein the contacting is carried out in the presence of dimethylsulfoxide, dimethylformamide, N-methylpyrrolidinone, acetonitrile, or triethanolamine.

9. The process of claim 1 wherein the aldehyde is citral, geranial, or neral.

10. The process of claim 1 wherein the aldehyde is cinnamaldehyde, piperonal, benzaldehyde, p-methoxybenzaldehyde, or 2,4-hexadienal.

11. The process of claim 1 wherein the aldehyde is the (3R)-enantiomer of citronellal, the (3S)-enantiomer of citronellal, or a mixture thereof.

12. The process of claim 1 wherein the molar ratio of ammonia or ammonium hydroxide to aldehyde is from about 0.5 to about 20.

13. The process of claim 1 wherein the molar ratio of ammonia or ammonium hydroxide to aldehyde is from about 0.9 to about 5.

14. The process of claim 1 wherein the molar ratio of ammonia or ammonium hydroxide to aldehyde is from about 1 to about 2.

15. The process of claim 1 wherein the molar ratio of hydrogen peroxide to aldehyde is from about 0.8 to about 50.

16. The process of claim 1 wherein the molar ratio of hydrogen peroxide to aldehyde is from about 1 to about 10.

17. The process of claim 1 wherein the contacting is performed by adding aldehyde, ammonia or ammonium hydroxide and hydrogen peroxide to a mixture of catalyst and solvent.

18. The process of claim 1 wherein the contacting is performed by adding ammonia or ammonium hydroxide and hydrogen peroxide to a mixture of aldehyde, solvent, and catalyst.

19. The process of claim 1 wherein:
   a. the contacting is performed by adding aldehyde, ammonia or ammonium hydroxide and hydrogen peroxide to a mixture of catalyst and solvent;
   b. addition of the aldehyde, ammonia or ammonium hydroxide, and hydrogen peroxide starts at about the same time;
   c. the addition of the aldehyde is completed first;
   d. the addition of the ammonia or ammonium hydroxide is completed second; and
   e. the addition of the hydrogen peroxide is completed third.

20. The process of claim 1 wherein the contacting is carried out at a temperature from about minus 10° C. to about plus 70° C.

21. The process of claim 1 wherein the contacting is carried out at a temperature from about 0° C. to about plus 45° C.

22. The process of claim 1 performed batch-wise.

23. The process of claim 1 performed continuously.

24. The process of claim 2 wherein R comprises from about 1 to about 40 carbons.

25. The process of claim 2 wherein R comprises from about 5 to about 20 carbons.

26. The process of claim 1 further comprising the subsequent step of removing the transition metal or transition metal compound from the reaction product by converting it into an insoluble or poorly soluble compound.

* * * * *

UNITED STATES PATENT AND TRADEMARK OFFICE
CERTIFICATE OF CORRECTION

PATENT NO. : 6,114,565
DATED : September 5, 2000
INVENTOR(S) : Mark B. Erman, et al.

It is certified that error appears in the above-identified patent and that said Letters Patent is hereby corrected as shown below:

Column 1,
Line 5, change "nitrites" to read -- nitriles --.
Line 8, change "nitrites" to read -- nitriles --.
Line 13, change nitrites" to read -- nitriles --.
Line 30, change "RCH=NHOH" to read -- RCH=NOH --.
Line 34, change "nitrites" to read -- nitriles --.
Line 43, change "nitrites" to read --nitriles --.
Line 48, change "dilsopropyl" to read -- diisopropyl --.
Line 51, change "nitrites" to read -- nitriles --.

Column 2,
Line 17, change "-H2O" to read -- -$H_2$ --.
Line 25, change "nitrites" to read -- nitriles --.
Line 67, change "nitrites" to read -- nitriles --.

Column 3,
Line 11, change "nitrites" to read -- nitriles --.
Line 28, change "nitrites" to read -- nitriles --.
Line 30, change "nitrites" to read -- nitriles --.
Line 33, change "nitrites" to read -- nitriles --.
Line 53, change "nitrites" to read -- nitriles --.
Line 55, change "hydrolyse" to read -- hydrolyze --.
Line 57, change "nitrites" to read -- nitriles --.

Column 5,
Line 31, change "about I" to -- about 1 --.

Column 7,
Line 30, change "nitrites" to read -- nitriles --.
Line 43, change "nitrites" to read -- nitriles --.

Column 9,
Line 18, change "aiiimonium" to read -- ammonium --.

UNITED STATES PATENT AND TRADEMARK OFFICE
CERTIFICATE OF CORRECTION

PATENT NO. : 6,114,565
DATED : September 5, 2000
INVENTOR(S) : Mark B. Erman, et al.

Page 2 of 2

It is certified that error appears in the above-identified patent and that said Letters Patent is hereby corrected as shown below:

Column 11,
Line 11, remove space between "solvent/water/" and "catalyst".

Table 6,
Last line of second column should read -- Undecylic aldehyde --

Claims,
Claim 1, change "nitrite" to read -- nitrile.
Claim 2, change "nitrite" to read -- nitrile.

Signed and Sealed this

Twenty-seventh Day of November, 2001

Attest:

*Nicholas P. Godici*

NICHOLAS P. GODICI
*Attesting Officer*     *Acting Director of the United States Patent and Trademark Office*